(12) United States Patent
Robbins

(10) Patent No.: US 6,228,048 B1
(45) Date of Patent: May 8, 2001

(54) COLONIC IRRIGATION APPARATUS AND METHOD

(75) Inventor: Mark Robbins, Englewood, CO (US)

(73) Assignee: CM Robbins Company Inc., Englewood, CO (US)

(*) Notice: Subject to any disclaimer, the term of this patent is extended or adjusted under 35 U.S.C. 154(b) by 0 days.

(21) Appl. No.: 09/178,375

(22) Filed: Oct. 23, 1998

(51) Int. Cl.⁷ .................................................. A61M 1/00
(52) U.S. Cl. .............................. 604/31; 604/27; 604/500
(58) Field of Search ................................ 604/27, 48, 65, 604/67, 73, 113, 114, 246, 247, 257, 271, 131, 151, 275–277, 30–36; 4/420, 420.1, 420.5, 443, 445

(56) References Cited

U.S. PATENT DOCUMENTS

| | | |
|---|---|---|
| 906,711 | 12/1908 | McClung et al. |
| 1,217,692 | 2/1917 | Bookman . |
| 1,317,851 | 10/1919 | Arnett . |
| 1,758,332 | 5/1930 | Pittam et al. . |
| 1,945,031 | 1/1934 | Decker .................................. 51/170 |
| 1,945,081 | 1/1934 | Ryan et al. ........................... 128/227 |
| 1,958,100 | 5/1934 | Borosini ............................... 128/227 |
| 2,027,588 | 1/1936 | Hannon ................................ 128/227 |
| 2,133,626 | 10/1938 | Mayberry ............................ 128/227 |
| 2,176,235 | 10/1939 | Woodard .............................. 128/227 |
| 2,252,569 | 8/1941 | Kennison ............................. 128/227 |
| 2,420,507 | 5/1947 | Stratton ............................... 128/227 |
| 2,506,183 | 5/1950 | Touchberry .......................... 128/33 |
| 2,564,135 | 8/1951 | Touchberry .......................... 311/9 |
| 2,955,596 | 10/1960 | Knoch .................................. 128/251 |
| 3,004,537 | 10/1961 | Turliuc ................................ 128/227 |
| 3,142,298 | 7/1964 | Koski et al. .......................... 128/276 |
| 3,401,694 | 9/1968 | Touchberry .......................... 128/227 |
| 3,678,932 | 7/1972 | Hudson ................................ 128/227 |
| 3,750,668 | 8/1973 | Perl ...................................... 128/227 |
| 3,771,522 | 11/1973 | Waysilk et al. ....................... 128/227 |
| 3,830,235 | 8/1974 | Marsan ................................. 128/227 |
| 4,187,057 | 2/1980 | Xanthopoulos ....................... 417/63 |
| 4,190,059 | 2/1980 | Holt ..................................... 128/750 |
| 4,262,239 | 4/1981 | Kawa ................................... 318/561 |
| 4,403,982 | 9/1983 | Clayton ................................ 604/28 |
| 4,504,270 | 3/1985 | Miller .................................. 604/275 |
| 4,518,382 | 5/1985 | Bloxom, Jr. ......................... 604/27 |
| 4,617,011 | 10/1986 | Bloxom, Jr. ......................... 604/27 |
| 4,626,239 | 12/1986 | Ardizzone ............................ 604/31 |
| 4,637,814 | 1/1987 | Leiboff ................................ 604/27 |
| 4,682,979 | 7/1987 | Girouard .............................. 604/48 |
| 4,790,811 | 12/1988 | Bloxom, Jr. ......................... 604/27 |
| 4,792,332 | 12/1988 | Lansel ................................. 604/276 |
| 4,842,580 | 6/1989 | Ouelette .............................. 604/30 |
| 4,874,363 | 10/1989 | Abell ................................... 604/28 |
| 4,893,634 | 1/1990 | Kulik et al. ......................... 128/748 |
| 5,019,056 | 5/1991 | Lee et al. ............................ 604/257 |
| 5,190,519 | 3/1993 | Mead et al. .......................... 604/27 |
| 5,309,899 | * 5/1994 | Ginsberg ............................. 604/38 |
| 5,405,319 | 4/1995 | Abell et al. .......................... 604/27 |
| 5,527,275 | * 6/1996 | Ginsberg ............................. 604/38 |
| 5,871,463 | * 2/1999 | Baker et al. ......................... 604/27 |
| 5,951,511 | * 9/1999 | Lowder ............................... 604/73 |

* cited by examiner

*Primary Examiner*—Manuel Mendez
(74) *Attorney, Agent, or Firm*—Sheridan Ross P.C.

(57) ABSTRACT

A colonic irrigation apparatus for cleaning bodily orifices such as the large intestine, which converts pressurized water from a building's water supply into a gravity flow and which provides precise temperature control even at extremely low flow rates. Water temperature is regulated by alternating the flow from separate hot and cold water inlets around a preset temperature set point, and sending the water into a filter. The filter blends the water, evening the temperature, whereupon the water passes through a temperature safety valve and on to an elevated pressure-to-gravity converter. Pressure is regulated by the converter, which receives the pressurized water, drains most of it under the flow of gravity to the patient at a preset flow rate, and vents the excess pressure by diverting a variable flow of the incoming water down to a drain.

26 Claims, 6 Drawing Sheets

COLONIC IRRIGATION APPARATUS AND METHOD

FIELD OF THE INVENTION

This invention relates generally to an apparatus for performing colon hydrotherapy, or colonic irrigation, and specifically to a colon hydrotherapy apparatus having precise water temperature control.

BACKGROUND OF THE INVENTION

Colonic irrigation is a process of cleansing the tissues of the lower intestine with water for purposes of removing impacted fecal material and other potentially toxic waste. Colonics are performed both as a preventive measure to sustain healthy digestion, peristalsis, and bowel tissue, and as a treatment for specific diseases such as colitis. Many of the problems addressed by colon hydrotherapy are associated with the typical "western" diet which is low in fiber, centered on meat, dairy, and processed foods, and which is poorly suited for the human digestive tract.

Medical devices have been employed in colonic irrigation for many years. For example, in 1935, U.S. Pat. No. 2,024,967 was issued for an apparatus to rehabilitate peristalsis of the colon. Over the years, colonic lavaging devices have evolved to include certain controls such as water temperature and pressure regulating devices, which ease administration of the colonic while insuring the comfort and safety of the patient. In the typical hydrotherapy procedure, the patient lies on her back or side, and a tube is inserted into the rectum. Fresh water flows into the bowel, loosening waste material from the walls of the colon and allowing the loosened waste material to flow out of the colon.

In the past two decades, colonic machines have reached a relatively high degree of refinement, as has the growing practice of colon hydrotherapy. More recent examples of prior art mechanisms and systems employed in colonic lavage may be seen in U.S. Pat. Nos. 4,190,059, 4,626,239, 4,682,979, and 4,842,580. While most devices are intended for professional use by a licensed colon hydrotherapist, devices have also been designed for home use, such as U.S. Pat. No. 4,645,497. Throughout the continuing evolution in hydrotherapy devices, two variables have remained key in delivering quality colonic treatment: water temperature and water pressure. Precise temperature control is important, not only for safety and comfort of the patient, but also because temperature can affect the peristaltic action of the bowel. Selecting the proper temperature, or alternating the temperature between warm and cool during the colonic, heightens the benefits of the procedure. Precise pressure control is important as excessive water pressure can cause pain and even injury.

Early colonic machines used hot and cold water from a building's plumbing system and simply used gravity to provide safe water pressure. The hot and cold water are passed through a mixing valve to achieve the desired temperature. Water is then delivered into an elevated tank or reservoir. From there, the water flows down naturally into a speculum and to the patient.

By the late 1970s, several problems had become apparent with this type of system. First, the reservoir, which may hold five or more gallons, makes the machine bulky and a more or less permanent installation. Second, precise temperature control is extremely difficult. If the reservoir is inadvertently filled with water that is too hot or too cold, the patient must wait either for the water to adjust on its own, or for the tank to be drained and refilled. Third, once the temperature in the reservoir is established, it cannot be easily varied during the course of the colonic. Fourth, the only way the pressure can be varied is by raising or lowering either the patient or the entire reservoir.

Later colonic machines, starting with U.S. Pat. No. 4,190,059, have addressed these problems by employing regulating valves to control water pressure. In such machines, hot and cold water still come from a building's plumbing system and are mixed through a thermostatically controlled mixing valve to achieve the desired temperature. However, one or more pressure regulating valves then keep the water pressure controlled within a certain range. While this method represents a major improvement over the earlier reservoir method, it too has several shortcomings. First, while temperature is certainly more controllable, water temperature through the mixing valve may still vary by a factor of several degrees. Second, the temperature of the water delivered during the procedure is vulnerable to pressure variances within the building's hot and cold water supply lines. Third, after nearly two decades of using such devices, a number of colon hydrotherapists and patients have come to perceive the earlier, gravity-pressure system as an inherently safer method. Their preference for this more natural type of pressure control is evidenced in part by continued sales and usage of the older reservoir systems, despite their numerous limitations. The present invention, therefore, is directed at alleviating all of these problems and limitations that are associated with both types of colonic irrigation machines of the prior art.

SUMMARY OF THE INVENTION

Objectives of the present invention include providing a colonic irrigation apparatus and method that provides for precise control of the temperature of the water to be delivered to the patient; that offers the benefits and safety of gravity pressurization without the disadvantages associated with machines that rely on bulky reservoirs or tanks; that is easy to set up, use, and adjust; that is highly compact and portable; that is versatile in that it may be used by professional colon hydrotherapists or by home users; and/or that can be used as a subcomponent of, or an attachment to, an existing colonic machine or as a complete system requiring only a colonic table or board. Related objectives include providing a hydrotherapy apparatus and method that provides a method of converting pressurized water from a building's plumbing system into a gravity pressurized flow, easily and conveniently, and provides a new method of controlling a temperature of water mixed from separate hot and cold water inflows, which is extremely precise, within 1° F., even at flow rates as low as 0.1 gallons per minute.

Further objects and advantages of the present invention will become apparent from a consideration of the drawings and ensuing description.

An apparatus for colonic irrigation is disclosed which features a new method of precisely regulating water temperature that far surpasses the technology used in any of the prior art and allows for gravity-pressurization, without the aforementioned limitations and bulk of a reservoir system. In one embodiment, the hydrotherapy apparatus includes:

determining means for determining a predetermined temperature for the lavaging liquid (e.g., a central processor, a user actuated control, etc.);

a temperature sensor (e.g., a thermister, a thermocouple, an RTD, etc.;

comparing means for comparing a first temperature of a first portion of a liquid with the predetermined temperature (e.g., a central processor, a comparator circuit, etc.), the comparing means being in communication with the determining means and the temperature sensor;

control means for generating a control signal (e.g., a central processor, a suitable electrical circuit, etc.) to contact second and/or third portions of the liquid with the first portion;

mixing means for mixing the first portion of the liquid with at least one of the second and third portions of the liquid to form an orifice irrigation liquid (e.g., a water filter, a baffled in line mixer, an impeller, etc.); and introducing means for introducing the orifice irrigation liquid into the bodily orifice (e.g., a speculum). When the first temperature is less than the predetermined temperature (e.g., the first portion is cold water), a second portion of the liquid having a second temperature more than the predetermined temperature (e.g., the second portion is hot water) is contacted with the temperature sensor. When the first temperature is more than the predetermined temperature (e.g., the first portion is cold water), a third portion of the liquid having a third temperature less than the predetermined temperature (e.g., the third portion is cold water) is contacted with the temperature sensor.

The apparatus has a number of attractive features. It is capable of controlling the temperature of the liquid, prior to use in a patient, to within about 1° F., even at flow rates as low as about 0.1 gallons per minute. It achieves this goal by employing separate hot and cold water inflows and precisely mixing the inflows to attain the predetermined temperature. Mixing is performed by injecting alternating streams of hot and cold liquid into the mixing device. In this manner, the apparatus is largely unaffected by sudden changes in water pressure from a building's hot and cold water inlets. In addition, it is easy to set up, use, and adjust; it is highly compact and portable; it is versatile; and it can be used as a subcomponent of, or an attachment to, an existing colonic machine.

The apparatus can include a second temperature sensor for measuring a fourth temperature of the orifice irrigation liquid. In that event, the predetermined temperature is either the sum of (i) the first temperature and (ii) the difference between a selected temperature (e.g., a temperature selected by a user) and the fourth temperature when the fourth temperature is substantially constant during a selected time interval. When the fourth temperature varies substantially during the selected time interval, the predetermined temperature is preferably the selected temperature.

The control signal(s) generated by the control means causes the temperature sensor to be first contacted with one of the second and third portions of the liquid and thereafter with the other of the second and third portions of the liquid. For example in a typical application, pulses of hot water and pulses of cold water are sequentially and alternately contacted with the temperature sensor in response to the control signal(s).

In the event of malfunction of the temperature control system, the apparatus can include means for determining if the fourth temperature is within a selected temperature range. If the fourth temperature is outside of the selected temperature range (i.e., either above the range or below the range), at least a portion of the liquid is redirected away from the speculum and maintained free of contact with the bodily orifice for the safety and comfort of the patient.

In operation, the apparatus performs the following steps:

(a) contacting the first portion of the liquid with the temperature sensor;

(b) comparing the first temperature with the predetermined temperature;

(c) when the first temperature is less than the predetermined temperature, thereafter contacting the second portion of the liquid having a second temperature more than the predetermined temperature with the temperature sensor and, when the first temperature is more than the predetermined temperature, thereafter contacting the third portion of the liquid having a third temperature less than the predetermined temperature with the temperature sensor;

(d) thereafter mixing the first portion of the liquid with at least one of the second and third portions of the liquid to form an orifice irrigation liquid; and (e) introducing at least a portion of the orifice irrigation liquid into a bodily orifice.

In yet another embodiment, the apparatus includes the following components:

a sensing module having (i) a first input for a cold liquid stream having a temperature less than the predetermined temperature, (ii) a second input for a hot liquid stream having a second temperature more than the predetermined temperature, (iii) a temperature sensor in communication with each of the first and second inputs, and (iv) an output;

a mixing device in communication with the output to form the orifice irrigation liquid; and a controller for comparing a temperature signal from the temperature sensor with the predetermined temperature and generating a control signal either to open the first input and close the second input to contact the cold liquid stream with the mixing device or to close the first input and open the second input to contact the hot liquid stream with the mixing device. The first and second inputs can be in an opposing relationship with the temperature sensor (and/or output) being located between the opposing inputs. The system can include a shutdown valve located downstream of the mixing device and a second temperature sensor in the event that the temperature of the orifice irrigation liquid is outside of the selected temperature range (in which event the shutdown valve is closed).

The apparatus can include a pressure-to-gravity converter that is directly connected to a building's water supply. The converter includes a reservoir or casing that is open to the atmosphere at the top, an input from the building's water supply in the middle, an overflow located above the input, and an output to the speculum located below the input and the overflow. In one configuration, the reservoir is tubular with the output to the speculum and the open end of the tube being located along the longitudinal axis of the tube. The pressure of the orifice irrigation liquid can be easily adjusted by adjusting the height of the reservoir. During use, it is preferred that sufficient water flow into the reservoir that a continuous stream of water flows through the overflow to a drain. In this manner, a continuous and constant pressure is applied to the patient.

The above-noted converter is a gravity-pressurized system having all the benefits and advantages of a pressure valve regulated apparatus, without a bulky reservoir and other disadvantages formerly associated with gravity pressurized devices. The pressure-to-gravity converter allows for direct connection to a building's water supply while still providing gravity flow. It is well suited to both professional and home use.

DETAILED DESCRIPTION OF THE INVENTION

Figure 1:
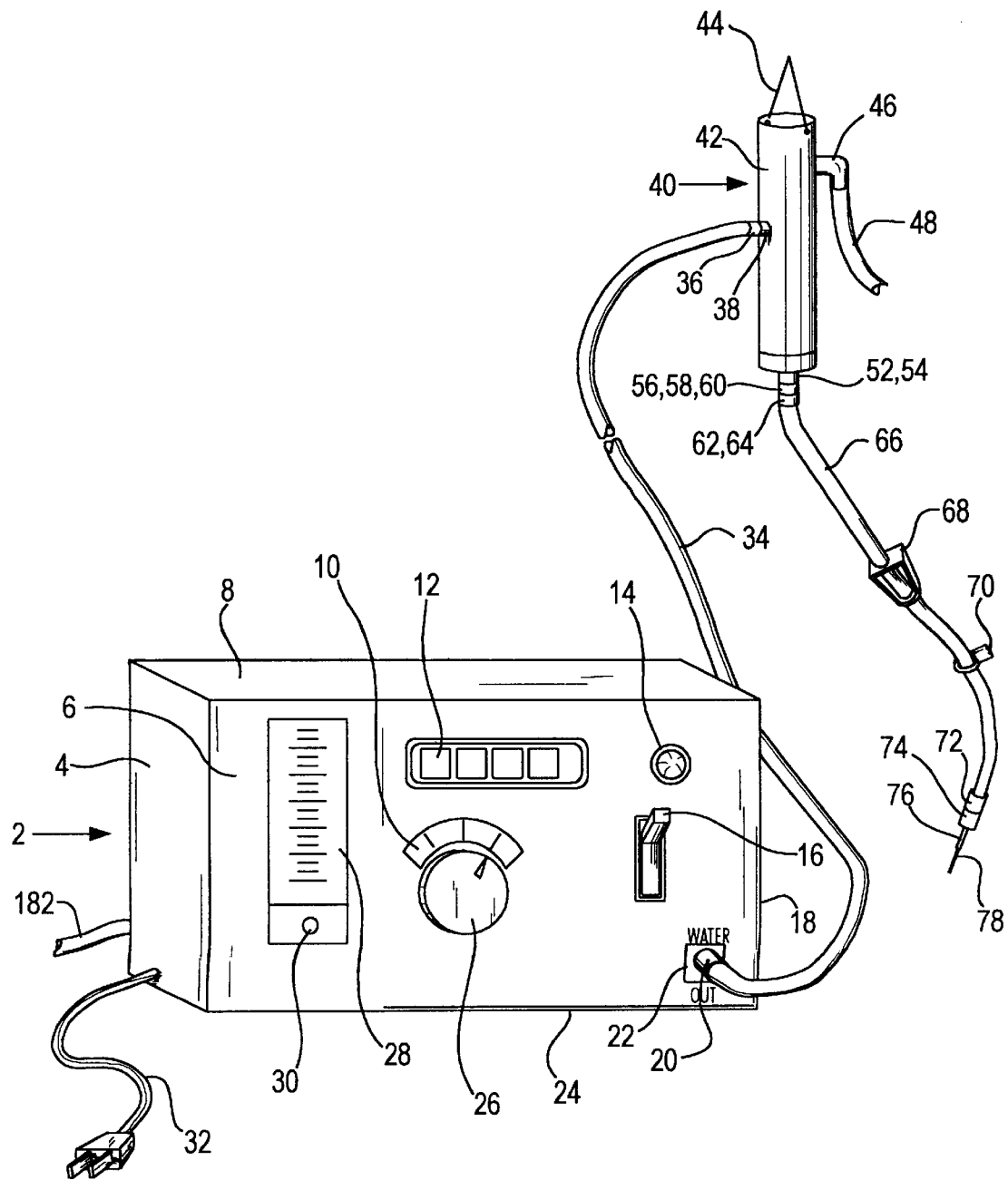
FIG. 1 is a front elevational view illustrating the two main components of the colonic irrigation apparatus which are the temperature and flow control device and the pressure-to-gravity converter.

FIG. 1 shows the colonic irrigation apparatus of the present invention. The two main components of this apparatus are a temperature and flow control device indicated generally by the reference numeral 2, and a pressure-to-gravity converter indicated generally by the reference numeral 40.

Figure 2:
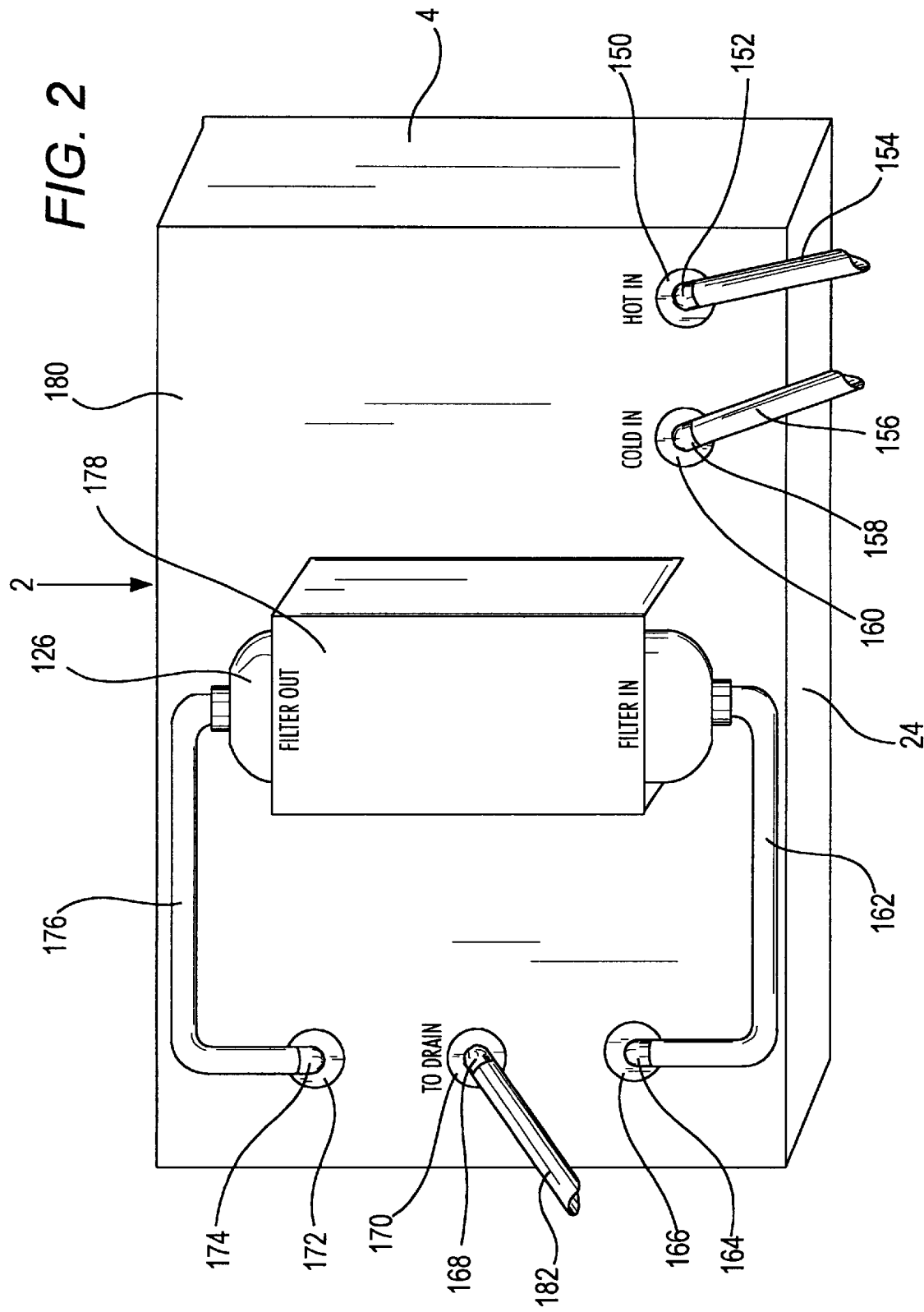
FIG. 2 is a rear view of the temperature and flow control device shown in FIG. 1, detailing the rear panel.

Beginning with temperature and flow control device 2 (FIG. 1), the device is enclosed by a front panel 6, left side panel 4 and right side panel 18, bottom panel 24, and a top panel 8. Device 2 also has a demountable back panel 180 that is shown in FIG. 2. The front panel 6 of device 2 (FIG. 1) features a standard flow gauge 28 with a needle valve 30. Front panel 6 also features a temperature range decal 10, and a digital temperature display 12. Front panel 6 also features a temperature set point potentiometer 26, an on/off switch 16, a temperature safe indicator light 14, and a water connector (female) 22 for outgoing water.

In FIG. 2, rear panel 180 of device 2 has a water connector 160 for incoming cold water, and a water connector 150 for incoming hot water. Connector 160 fastens to quick connect (male) 158, which is attached to tube 156. Connector 150 fastens to quick connect (male) 152, which is attached to tube 154. Tubes 154 and 156 are suitably adapted for connection to pressurized hot and cold water sources (not shown), such as conventional faucets or a building's water supply system.

The rear panel 180 also features houses a connector 166 through which water can exit device 2. Connector 166 fastens to a quick connector (male) 164, which is attached to a tube 162. Tube 162 connects to a water filter 126, which is housed in a filter compartment 178. In the preferred embodiment, the water filter 126 is a KDF-55 filter, model R/O DeChlorinator (made by: Aqua Freshe Inc., P.O. Box 40, Prairie Hill, Tex. 76678). Water exiting the filter 126 passes through a tube 176 which is attached to a quick connect (male) 174. Quick connect 174 fastens into a connector 172 allowing water to return into the device 2. Finally, rear panel 180 houses a connector 170, which fastens to a quick connect (male) 168. Quick connect 168 is attached to a tube 182 through which water may exit device 2 and flow to a drain.

Leading in through back panel 180 to the interior components of temperature and flow control device 2 (FIG. 3), hot and cold water connectors 150 and 160 attach to a tube 110 and a tube 96 respectively. The tubes 110 and 96 connect to a hot water valve 112 and a cold water valve 98, respectively. The valves 112 and 98 each contain an electrical coil, 114 and 100 respectively. The coils 114 and 100 are each connected by a pair of electrical wires 106 and 92 respectively, to a circuit board 86. The valves 112 and 98 each connect to a tube 116 and a tube 102 respectively. The tubes 116 and 102 lead hot and cold water into opposite ends of a female cross 120. A thermistor 118 (T1) is inserted into a third end of cross 120, such that it sits in the middle of the cross, exposed to hot and cold water coming from tubes 116 and 102 on either side. The thermistor 118 is connected by a suitable pair of electrical wires 104 to a circuit board 86. The circuit board 86 is connected via a pair of electrical wires 82 to a 12 volt power supply 80, which plugs into any standard AC outlet via a cord and plug 32. The circuit board 86 is directly connected to the potentiometer 26, the on-off switch 16, the safety light 14, and the digital display 12. The circuit board 86 also houses a signal conditioner 90, a set of power drivers 88, and a microprocessor 84.

Returning to the female cross 120, the remaining end of the cross is connected to a tube 122. The tube 122 carries water through a standard flow control valve 30 and flow meter 28. Water leaves the meter 28 through a tube 124. The tube 124 is attached to the connector 164, which is fixed into the rear panel 180 (not shown in FIG. 3). The connector 164 attaches to the quick connect 166 which is attached to the tube 162. The tube 162 connects to the water filter 126. Water exiting the filter 126 passes through the tube 176 which is attached to the quick connect (male) 174. The quick connect 174 fastens into the connector 172 which is fixed into the rear panel 180 of the device 2.

The connector 172 is attached to a tube 128, which directs the water to a female "T" 130. The female "T" 130 houses a thermistor 132 (T2), which is connected via a suitable pair of electrical wires 134 to the circuit board 86. Water leaves the female "T" 130 via a tube 138, and enters a fail safe valve 146. The valve 146 contains an electrical coil 140, which is connected via a pair of electrical wires 136 to the circuit board 86. If the valve 146 is closed, water flows out of the rear panel 180 of the device 2 via a tube 142 and to a drain (not shown). If the valve 146 is open, water flows through a tube 148, out of the front panel 6 of the device 2, on its way to the pressure-to-gravity converter 40.

Figure 3:
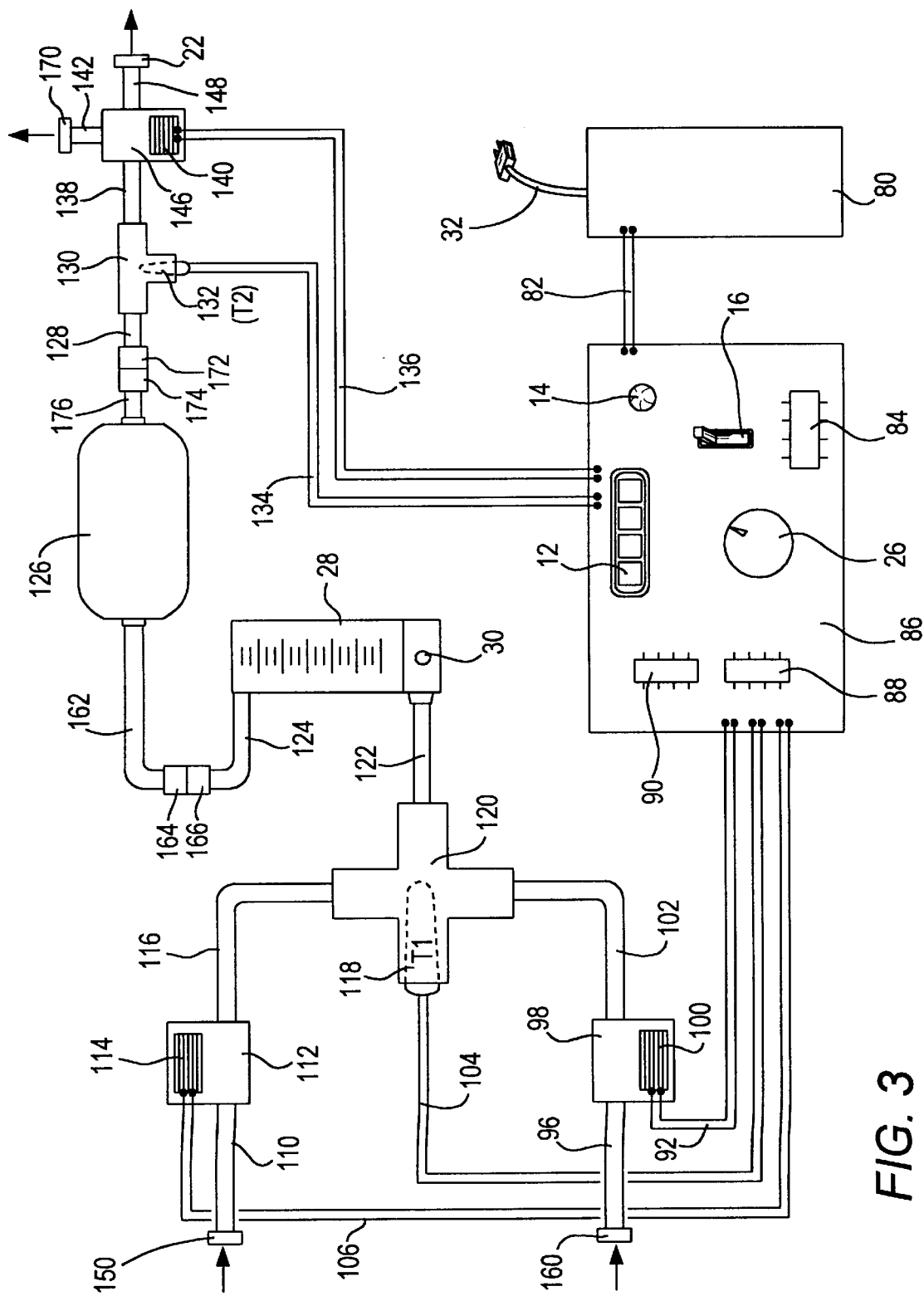
FIG. 3 is a block diagram of the internal components of the temperature and flow control device shown in FIGS. 1 and 2.
Figure 4:
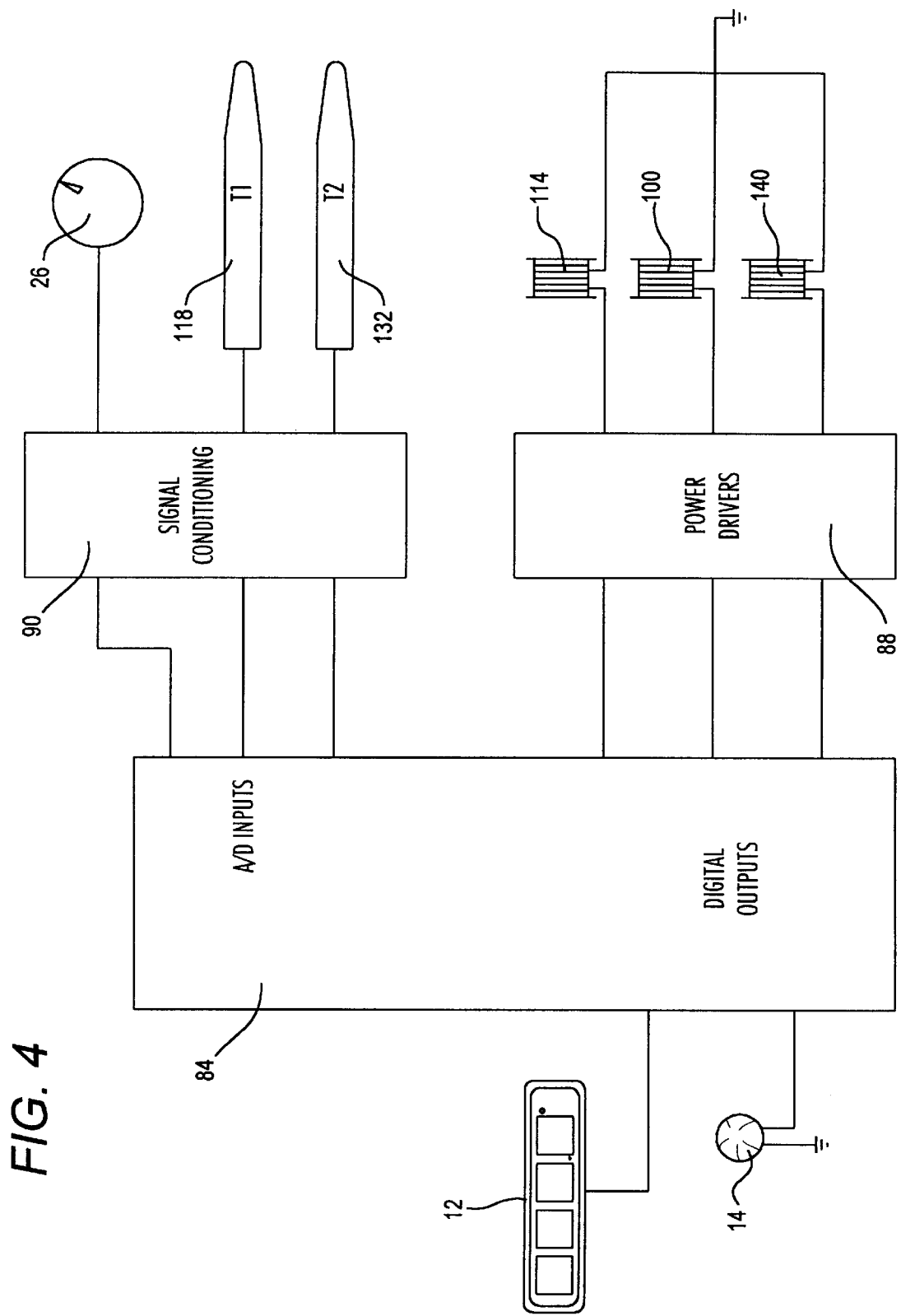
FIG. 4 is a block diagram of the electronic elements of the temperature and flow control device shown in FIGS. 1 and 2.

The electronics of the temperature and the flow control device 2 are illustrated by FIG. 4. Beginning at the right side of FIG. 4, temperature readings run from the potentiometer 26, and from the thermistors 118 and 132, to the circuit board 86 (shown in FIG. 3). The circuit board 86 houses and connects the signal conditioner 90, the processor 84, and the power drivers 88. The signal conditioner 90 comprises a precision voltage regulator and a series of precision resistors that are arranged to convert the resistance of the thermistors 118 and 132 into voltage. Signals from the potentiometer 26, the thermistor 118, and the thermistor 132, pass through the signal conditioner 90 where they are converted into binary code, and then relayed to the processor 84.

The processor 84 is encoded with programming (described below and depicted in FIG. 5) which controls the digital outputs sent to the temperature display 12, the temperature safe indicator light 14, and the power drivers 88. The power drivers 88 amplify outputs from the processor 84 and send corresponding signals to the electronic coils 114, 100, and 140.

Figure 5:
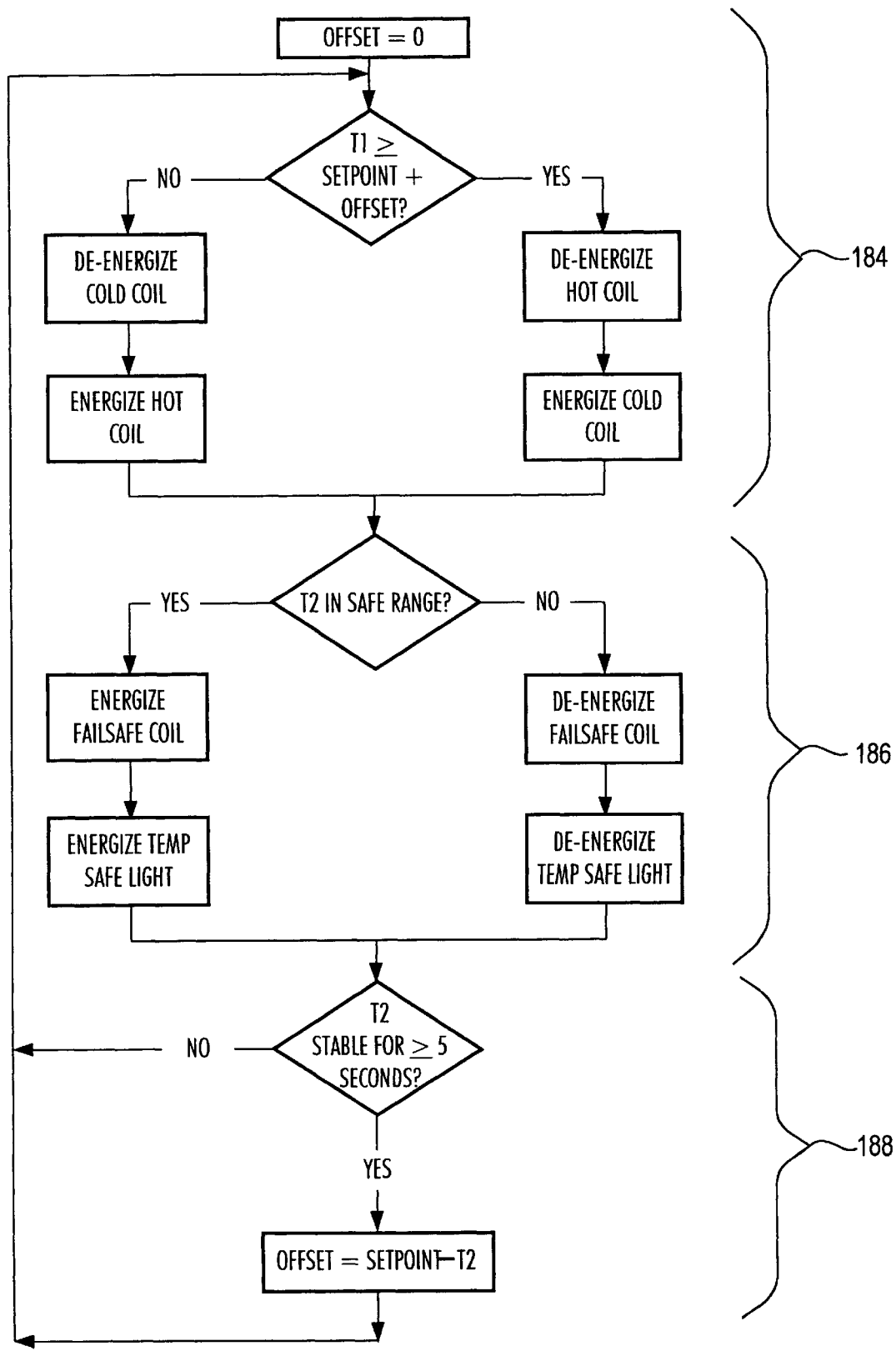
FIG. 5 is a flow chart of software that controls temperature regulation and safety in the temperature and flow control device shown in FIGS. 1 and 2.

Moving now to FIG. 5, software programming contained in the processor 84 (FIG. 4) is indicated and distinguished generally by the reference numerals 184, 186, and 188. The software 184 first sets an offset to zero. The software 184 then compares the voltage received from the thermistor 118

(FIG. 3) to the voltage received from the potentiometer 26. If the voltage from the thermistor 118 is greater than or equal to voltage from the potentiometer 26, the software 184 causes an appropriate signal to be sent to de-energize the electronic coil 114 (hot) and to energize the electronic coil 100 (cold). If the voltage from the thermistor 118 is less than the voltage from the potentiometer 26, the software 184 causes an appropriate signal to be sent to energize the electronic coil 114 (hot) and de-energize the electronic coil 100 (cold). Thus, the software 184 generally serves to control the operation of the hot and cold water valves 112 and 98 (FIG. 3). The software 184 thus regulates the inflow of hot and cold water into the female cross 120 (FIG. 3). The software 186 generally controls the operation of the fail safe valve 140 (FIG. 3). The software 186 determines whether the voltage from the thermistor 132 is within a preset range corresponding to a temperature range of about 83° F. to about 103° F. If the voltage from the thermistor 132 is not within this preset range, the software 186 causes an appropriate signal to be sent to de-energize the failsafe coil 140 and the temperature safe indicator light 14. If the voltage from the thermistor 132 is within this preset range, the software 186 causes an appropriate signal to be sent to energize the failsafe coil 140 and the temperature safe indicator light 14.

The software 188 serves to correct for discrepancies between the voltage from the potentiometer 26 and from the thermistor 132 by way of the signal conditioner 90 (FIG. 3). If the reading from the thermistor 132 does not vary by 0.3° F. for at least five seconds, the software 188 assigns a value to an offset equal to the difference between the voltage from the potentiometer 26 and the voltage from the thermistor 132 by way of the signal conditioner 90. The offset value in the software 188 is then added to the setpoint value in the software 184.

Figure 6:
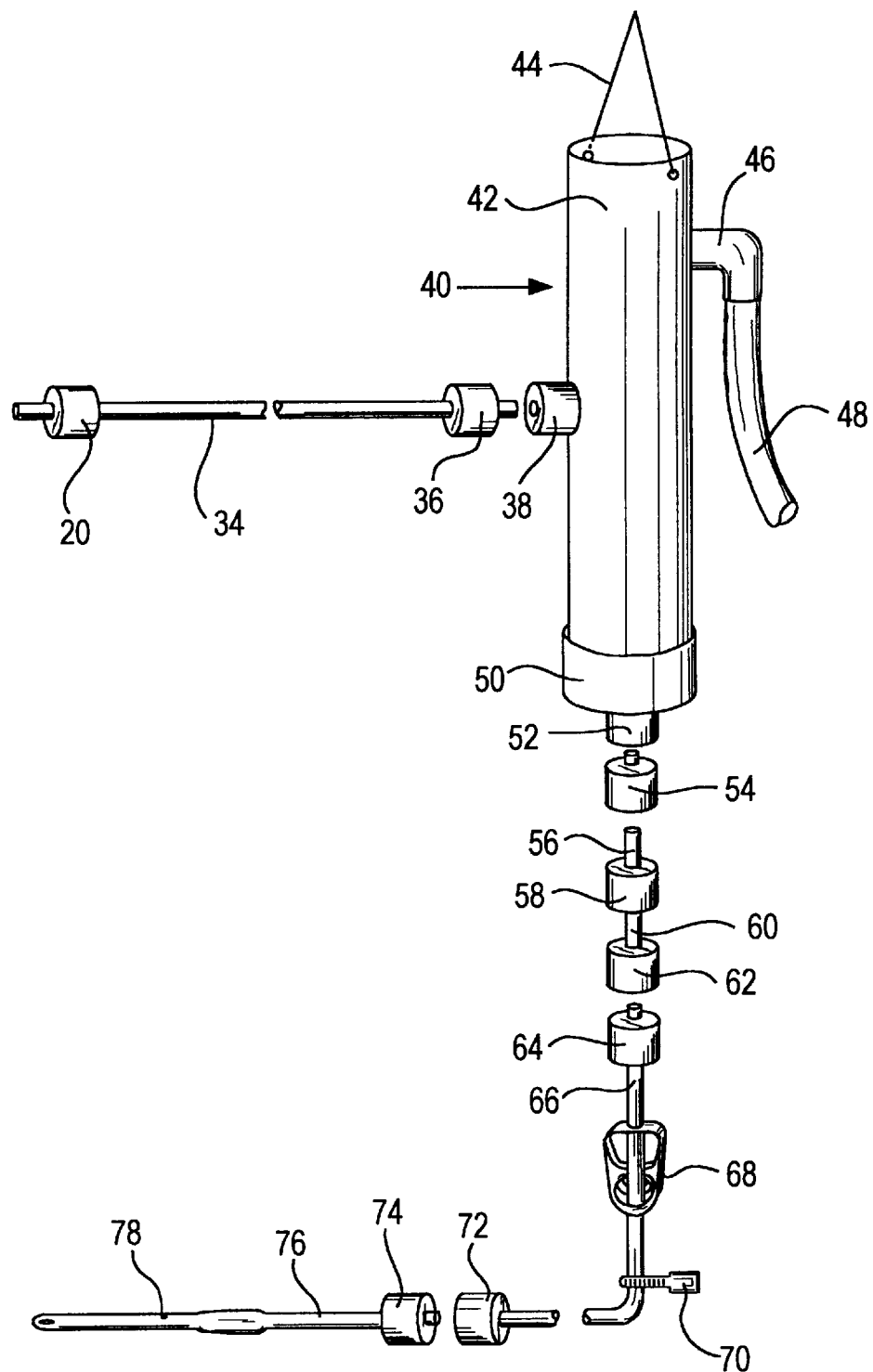
FIG. 6 is a detailed view of the pressure-to-gravity converter mechanism shown in FIG. 1.

Moving to the pressure-to-gravity converter mechanism 40 shown in FIG. 6, the male quick connector 20 connects the tube 34 to the water connector 22 which is fixed in the front panel 6 of the device 2 (shown in FIG. 1). Water flows through the tube 34, which ends with a male quick connector 36. The quick connector 36 inserts into a one-eighth inch diameter female quick connector 38. The connector 38 fits tightly into a hole in the side of an outer casing 42, which is the main component of the pressure-to-gravity converter 40. The preferred embodiment of the casing 42 is a 12" length of 1" O.D.(nominal) schedule 40 PVC pipe. The casing 42 is open at the top, and a nylon cord 44 is affixed in a suitable manner to opposite sides of the opening such that the converter 40 may be hung from a hook (not shown) and suspended at a desired height. A one-half inch diameter barbed elbow connector 46 protrudes from the side of casing 42. The elbow connector 46 is situated at a level between the top opening of the casing 42 and the female quick connector 38, and on the opposite side from the connector 38. The elbow connector 46 attaches to a tube 48, which has an inner diameter at least two-eighths of an inch wider than the tube 34. The opposite end of the tube 48 is open, and flows to a sink or drain (not shown), or may be permanently connected by suitable means to a drainpipe (not shown).

The bottom of the casing 42 is sealed with an end cap 50. From the bottom of the end cap 50, through a hole drilled in the cap, protrudes a female quick connector 52 which connects to a male quick connector 54, which connects to a tube 56, which connects to a standard check valve 58. The check valve 58 connects to a tube 60, which connects to a female quick connector 62, which connects to a male quick connector 64, which is attached to a tube 66. A hose clamp 68 rests on the tube 66, which is at least six feet in length. The tube 66 runs through a standard pinch valve 70, and ends with a female quick connector 72. The connector 72 attaches to a male quick connector 74. The connector 74 attaches to a ⅜" O.D. by ¼" I.D tube 76, which has a standard rectal tip (or speculum) 78 pushed into it. In the preferred embodiment, the speculum 78 is made by Ultimate Trends, PO Box 1427, Sandy, Utah 84091-1427.

It thus is seen that a colonic irrigation system is now provided which overcomes problems associated with those of the prior art. It should be understood, however, that the above-described embodiment merely illustrates principles of the invention in one preferred form. Many modifications, additions and deletions may, of course, be made thereto without departure from the spirit and scope of the invention as set forth in the following claims.

In normal operation of this invention, the hot and cold water tubes 154 and 156 are connected respectively by suitable means to a building's hot and cold water outlets. The pressure-to-gravity converter 40 is hung from a suitable hook approximately six feet above the floor. The tube 48 and the tube 182 are both connected (or directed) to a drain. The AC power cord 32 is plugged into a convenient AC outlet. Power is turned on via the on-off switch 16, and the temperature setpoint potentiometer 26 is set to the desired temperature (thus determining the temperature setpoint). The temperature setting is displayed by the digital temperature display 12. The hot and cold water outlets are turned on, and water flow rate is adjusted via the flow control needle valve 30 so that a moderate trickle of water is draining at all times from the pressure-to-gravity converter 40, through the tube 48, and into a drain pipe or sink, while water constantly flows out of the speculum 78.

Hot and cold water enters through the tubes 110 and 96 and passes through the hot and cold valves 112 and 98, and into the female cross 120. The valves 112 and 98 have only two possible positions: fully opened or fully closed. At the cross 120, the hot and cold water contacts the thermistor 118 (T1) from opposite sides. The thermistor 118 sends water temperature readings in the form of voltage to the signal conditioner 90 via the circuit board 86. The voltage from the thermistor 118 enters the signal conditioner 90 where it is converted into binary code, and then passed on via the circuit board 86 to the processor 84. Based on the software 184, if the temperature is too high relative to the desired temperature setpoint, the cold water valve 98 is opened and the hot water valve 112 is closed, such that only cold water enters the system and flows to the thermistor 118. The thermistor 118 cools and passes below the setpoint, whereupon, based on the software 184, the cold water valve 98 is closed and the hot water valve 112 is opened, such that only hot water enters the system and flows over the thermistor 118. This process continues back and forth constantly, as the hot and cold water hit thermistor 118 from opposite sides. The hot and cold water valves 112 and 98 are rapidly opened and closed in alternating sequence, creating short, alternating bursts of hot and cold water, which keep the average temperature read by the thermistor 118 approximately equal to the temperature setpoint.

The alternating bursts of hot and cold water flow from the female cross 120, through the flow meter 28 and then into the water filter 126, where they are thoroughly blended and mixed to an even temperature, which varies no more than +/−0.3° F., and which is within 10° F. of the setpoint. The blended water then exits the filter 126 and flows to the female "T" 130, where it contacts the thermistor 132 (T2). The thermistor 132 sends a temperature reading, in the form of voltage, to the signal conditioner 90, where it is converted into binary code. This code enters the processor 84 and activates the software 186. If the water temperature is not within the preset safety range (above 83° F. or below 103° F.) the software 186 causes a signal to be sent to the power drivers 88 which cause the electric coil 140 to be de-energized, closing the failsafe valve 146. The water flowing from the female "T" 130 is diverted via the tube 142, through the water connector (female) 170, through the tube 182, and to a drain or sink (not shown). The temperature safety indicator light 14 is caused to go out. If the water temperature is within the preset safety range, the software 186 causes a signal to be sent to the power drivers 88 which cause the electric coil 140 to remain energized, keeping the failsafe valve 146 open. The flowing water continues via the tube 148 through the water connector (female) 22, to the pressure-to-gravity converter 40 via the tube 34. The temperature safety indicator light 14 is caused to stay on.

Via the software 188 in the processor 84, the temperature of the outgoing water, as read by the thermistor 132 (T2), is constantly checked against and compared to the desired temperature setpoint. So long as the temperature is stable for at least five seconds, an offset is assigned a value equal to the difference between the temperature at the thermistor 132 (T2) and the temperature setpoint. This offset is then added to the setpoint value in the software 184. Thus, this feedback loop constantly adjusts and fine tunes the temperature reading at the thermistor 118 (T1) so that the desired temperature setpoint (indicated by the digital display 12) and the actual temperature of water leaving the system, measured by the thermistor 132 (T2), are equal to each other within 0.3° F.

The water leaves the device 2 and enters the pressure-to-gravity converter 40 at the precise temperature desired, regardless of temperature or pressure changes in the building's water supply. The water flows out the bottom of the casing 42, through a hole in the end cap 50, under gravity pressure. The water flow has been set via the needle valve 30 so that the water fills the casing 42 slightly faster than it drains out the hole. Excess water rises to the level of the barbed elbow connector 46, and vents out to a drain via the tube 48. Thus, regardless of sudden pressure changes in the building's water supply, water always flows out the bottom of the casing 42, to the patient, under a constant, gentle gravity flow. Any pressure differentials only affect the water which vents to the drain via the tube 48.

The patient momentarily closes the clamp 68 to seal off the tube 66, and the speculum 78 is carefully inserted into the anus. The patient then releases the clamp 68 to start the flow of water into the colon. Under gravity flow, water travels down through the check valve 58 and the tube 66 to the speculum 78 and into the patient. Water pressure can be varied, simply by raising or lowering the pressure-to-gravity converter 42.

While the above description contains many specificities, these should not be construed as limitations on the scope of the invention, but rather as an exemplification of one preferred embodiment thereof. Other variations are possible. For example, the rubber tubing could be made from solid pipe, or the casing could be made from wood or plastic instead of metal. The temperature control device could be made from analog circuitry as opposed to digital. Various types of temperature sensors could be used in place of thermistors. Also, the temperature control device could be used for other applications besides colonic irrigation, such as other medical procedures or industrial processes in which precise temperature control of flowing water is required. Accordingly, the scope of the invention should be determined not by the embodiment illustrated, but by the appended claims and their legal equivalents.

What is claimed is:

1. A method for controlling the temperature of a liquid used for irrigating a bodily orifice, comprising:
    (a) contacting a first liquid with a temperature sensor;
    (b) comparing a first temperature measured by the temperature sensor with a predetermined temperature;
    (c) when the first temperature is less than the predetermined temperature, thereafter contacting a second liquid having a second temperature that is more than the predetermined temperature with the temperature sensor and, when the first temperature is more than the predetermined temperature, thereafter contacting a third liquid having a third temperature less than the predetermined temperature with the temperature sensor;
    (d) thereafter mixing the first liquid with at least one of the second and third liquids to form an orifice irrigation liquid; and
    (e) introducing at least a portion of the orifice irrigation liquid into a bodily orifice.

2. The method of claim 1, further comprising:
    (f) measuring a fourth temperature of the orifice irrigation liquid prior to the introducing step.

3. The method of claim 2, wherein in the comparing step (b) the predetermined temperature is the sum of (i) the first temperature and (ii) the difference between a selected temperature and the fourth temperature.

4. The method of claim 2, wherein in the comparing step (b) the predetermined temperature is the selected temperature when the fourth temperature varies substantially during a selected time interval and the predetermined temperature is the sum of (i) the first temperature and (ii) the difference between a selected temperature and the fourth temperature when the fourth temperature is substantially constant during the selected time interval.

5. The method of claim 1, wherein the first, second, and third liquids are water, at least two of which have different temperatures, and step (c) comprises first contacting the temperature sensor with one of the second and third liquids and thereafter contacting the temperature sensor with the other of the second and third liquids.

6. The method of claim 2, further comprising:
    (g) determining if the fourth temperature is within a selected temperature range and
    (h) when the fourth temperature is outside of the selected temperature range, maintaining a portion of the orifice irrigation liquid free of contact with the bodily orifice.

7. A system for controlling the temperature of a liquid used for irrigating a bodily orifice, comprising:
    determining means for determining a predetermined temperature;
    a temperature sensor for measuring a temperature of a liquid in contact with the temperature sensor;
    comparing means for comparing a first temperature measured by the temperature sensor when in contact with a first portion of the liquid with the predetermined temperature, the comparing means being in communication with the determining means and the temperature sensor;
    control means for generating a control signal, wherein, when the first temperature is less than the predetermined temperature, a second portion of the liquid having a second temperature more than the predetermined temperature is contacted with the temperature sensor;

mixing means for mixing the first portion of the liquid with the second portion of the liquid to form an orifice irrigation liquid; and introducing means for introducing the orifice irrigation liquid into the bodily orifice.

8. The system of claim 7, wherein, when the first temperature is more than the predetermined temperature, a third portion of the liquid having a third temperature less than the predetermined temperature is contacted with the temperature sensor and wherein the liquid is water, at least two of the first, second, and third portions of which have different temperatures, and further comprising:

a second temperature sensor for measuring a fourth temperature of the orifice irrigation liquid.

9. The system of claim 8, wherein the predetermined temperature is the sum of (i) the first temperature and (ii) the difference between a selected temperature and the fourth temperature.

10. The system of claim 8, wherein the predetermined temperature is the selected temperature when the fourth temperature varies substantially during a selected time interval and the predetermined temperature is the sum of (i) the first temperature and (ii) the difference between a selected temperature and the fourth temperature when the fourth temperature is substantially constant during the selected time interval.

11. The system of claim 8, wherein the control signal causes the temperature sensor to be first contacted with one of the second and third portions of the liquid and thereafter to be contacted with the other of the second and third portions of the liquid.

12. The system of claim 8, further comprising:

means for determining if the fourth temperature is within a selected temperature range such that when the fourth temperature is outside of the selected temperature range, a portion of the liquid is diverted from contact with the bodily orifice.

13. A system for controlling the temperature of a liquid used for irrigating a bodily orifice, comprising:

a sensing module having a first input for a first portion of the liquid having a first temperature less than a predetermined temperature, a second input for a second portion of the liquid having a second temperature more than the predetermined temperature, a temperature sensor in communication with each of the first and second inputs, and an output;

a mixing device in communication with the output to mix the first and second portions and form the irrigation liquid; and a controller for comparing a temperature signal from the temperature sensor with the predetermined temperature and generating a control signal to open the first input and close the second input to contact the first portion of the liquid with the mixing device or close the first input and open the second input to contact the second portion of the liquid with the mixing device.

14. The system of claim 13, wherein the liquid is water, at least two of the first and second portions of the liquid, and a third portion of the liquid have different temperatures, and further comprising:

a second temperature sensor in communication with the mixing device for measuring a temperature of the irrigating liquid.

15. The system of claim 13, wherein the first and second inputs are in an opposing relationship and the temperature sensor is located between the first and second inputs.

16. The system of claim 14, further comprising:

a diversion valve located downstream of the mixing device and the second temperature sensor and wherein the controller generates a second control signal when the second temperature is outside of a selected temperature range to alter the state of the diversion valve.

17. The system of claim 13, further comprising:

a pressure-to-gravity converter including a tubular body having an input for the irrigation liquid, an overflow, an outlet to the atmosphere, and an outlet to a device for introducing the irrigation liquid into a bodily orifice, wherein the input is located below the output to the atmosphere and the overflow and above the output to the introducing device.

18. A method for controlling the flow of a liquid used for irrigating a bodily orifice, comprising:

(a) transporting an irrigation liquid;

(b) during the transporting step, measuring a temperature of the irrigation liquid with a temperature sensor;

(c) comparing the temperature of the irrigation liquid with a first predetermined temperature; and (d) when the temperature is less than the first predetermined temperature, thereafter diverting the irrigation liquid away from the bodily orifice to a waste outlet.

19. The method as claimed in claim 18, wherein the first predetermined temperature is a lower temperature threshold of a predetermined temperature range and a second predetermined temperature is the upper temperature threshold of the predetermined temperature range and further comprising:

when the temperature of the irrigation liquid is more than the second predetermined temperature, thereafter diverting the irrigation liquid away from the bodily orifice to the waste outlet.

20. The method of claim 18, further comprising:

(e) measuring a first temperature of a temperature sensor in contact with a first portion of the irrigation liquid;

(f) comparing the first temperature to a second predetermined temperature;

(g) when the first temperature is less than the second predetermined temperature, contacting a second portion of the irrigation liquid with the temperature sensor; and (h) thereafter combining the first and second liquids to form the irrigation liquid.

21. A method for controlling the temperature of a liquid used for irrigating a bodily orifice, comprising:

contacting a first portion of a liquid with a temperature sensor;

comparing a first temperature measured by the temperature sensor with a determined temperature;

when the first temperature is less than the determined temperature or when the first temperature is more than the determined temperature, contacting a second portion of the liquid having a temperature different from the first portion of the liquid with the temperature sensor;

thereafter combining the first portion of the liquid with the second portion of the liquid to form an orifice irrigation liquid; and introducing at least a portion of the orifice irrigation liquid into a bodily orifice.

22. The method of claim 21, further comprising:

measuring a second temperature of the orifice irrigation liquid prior to the introducing step.

23. The method of claim 22, wherein in the comparing step the determined temperature is the sum of (i) the first temperature and (ii) the difference between a selected temperature and the second temperature.

24. The method of claim 22, wherein in the comparing step the determined temperature is the selected temperature when the second temperature varies substantially during a selected time interval and the determined temperature is the sum of (i) the first temperature and (ii) the difference between a selected temperature and the second temperature when the second temperature is substantially constant during the selected time interval.

25. The method of claim 1, wherein the first and second liquid portions are water having different temperatures.

26. The method of claim 22, further comprising:

determining if the second temperature is within a selected temperature range and when the second temperature is outside of the selected temperature range, diverting a portion of the orifice irrigation away from the bodily orifice.

* * * * *